United States Patent
Tomkoria

(10) Patent No.: US 9,730,475 B1
(45) Date of Patent: Aug. 15, 2017

(54) BRASSIERE ACCESSORY FOR IMPROVING POSTURE

(71) Applicant: Anita Tomkoria, Newport Coast, CA (US)

(72) Inventor: Anita Tomkoria, Newport Coast, CA (US)

(*) Notice: Subject to any disclaimer, the term of this patent is extended or adjusted under 35 U.S.C. 154(b) by 0 days.

(21) Appl. No.: 15/376,373

(22) Filed: Dec. 12, 2016

(51) Int. Cl.
| | |
|---|---|
| *A41C 3/02* | (2006.01) |
| *A41C 3/00* | (2006.01) |
| *A41C 3/12* | (2006.01) |
| *A61F 5/01* | (2006.01) |

(52) U.S. Cl.
CPC ............ *A41C 3/005* (2013.01); *A41C 3/0007* (2013.01); *A41C 3/02* (2013.01); *A41C 3/12* (2013.01); *A61F 5/01* (2013.01)

(58) Field of Classification Search
CPC ........ A41F 15/02; A41F 19/005; A41F 19/00; A41C 1/00; A41C 3/00
USPC .... 450/54, 86, 85, 75; 2/310–312, 338, 336, 2/320–327
See application file for complete search history.

(56) References Cited

U.S. PATENT DOCUMENTS

| | | | | |
|---|---|---|---|---|
| 1,401,227 A | * | 12/1921 | Wyeth | A41F 15/02 2/323 |
| 1,648,776 A | * | 11/1927 | McOrin | A41F 15/02 2/323 |
| 1,782,057 A | * | 11/1930 | Bollinger | A41F 19/005 2/323 |
| 2,131,707 A | | 9/1936 | Leonard | |
| 2,137,563 A | * | 11/1938 | Caraway | A41F 19/00 184/27.1 |
| 2,736,899 A | | 5/1953 | Ayres | |
| 2,739,315 A | | 5/1954 | Heliotis | |
| 3,672,004 A | | 6/1972 | Smith | |
| 4,858,249 A | | 8/1989 | Stewart | |
| 5,149,293 A | | 9/1992 | Gable | |
| 5,558,556 A | | 9/1996 | Froehlich | |
| D383,888 S | | 9/1997 | Smith | |
| 5,662,512 A | | 9/1997 | Cohen | |
| 5,823,851 A | | 10/1998 | Dicker | |
| 6,006,364 A | * | 12/1999 | Newsom | A41F 15/02 2/323 |
| 6,038,745 A | | 3/2000 | Rapp | |
| 6,059,634 A | | 5/2000 | Fildan | |
| 6,135,853 A | * | 10/2000 | Hopson | A41F 15/02 2/323 |
| D433,650 S | * | 11/2000 | Gable | D11/200 |

(Continued)

FOREIGN PATENT DOCUMENTS

| | | |
|---|---|---|
| CA | WO03051242 | 6/2003 |
| CA | WO2015125448 | 8/2014 |
| WO | WO2014125448 | 8/2014 |

OTHER PUBLICATIONS

US 9,113,662, 08/2015, Mckeen (withdrawn)

*Primary Examiner* — Gloria Hale
(74) *Attorney, Agent, or Firm* — Jafari Law Group, Inc.

(57) ABSTRACT

The invention is a brassiere accessory for improving posture, and more specifically, to a brassiere accessory that couples to and between shoulder straps at the posterior portion of a brassiere. The brassiere accessory rests against the back of a user providing a supportive tension that prevents excessive kyphosis (curvature) of the thoracic spine (upper back) and straightens the back of the user so that the user's posture is improved.

20 Claims, 7 Drawing Sheets

(56) References Cited

U.S. PATENT DOCUMENTS

| | | | |
|---|---|---|---|
| 6,163,937 | A | 12/2000 | McKinnis et al. |
| 6,179,687 | B1 | 1/2001 | Lee et al. |
| 7,278,900 | B1 | 10/2007 | Ostaseski |
| 7,343,648 | B2 * | 3/2008 | Shaw .................. B60P 7/0823 24/265 CD |
| 7,410,407 | B2 | 8/2008 | Krammel |
| 8,241,090 | B2 | 8/2012 | Michael |
| 8,337,275 | B2 | 12/2012 | Martins-Crawbuck et al. |
| 8,864,549 | B2 | 10/2014 | Mckeen |
| 9,237,772 | B2 | 1/2016 | Mckeen |
| 9,392,822 | B2 | 7/2016 | Mckeen |
| 2007/0161329 | A1 | 7/2007 | Torrey |
| 2009/0126084 | A1 | 5/2009 | Fenske |
| 2011/0191944 | A1 | 8/2011 | Lescom et al. |
| 2011/0275277 | A1 | 11/2011 | Martins-Crawbuck et al. |
| 2014/0336555 | A1 | 11/2014 | Barbosa |
| 2015/0374266 | A1 | 12/2015 | Cohen et al. |
| 2016/0015090 | A1 | 1/2016 | Mazourik et al. |
| 2016/0150833 | A1 | 6/2016 | Spicer |

* cited by examiner

BRASSIERE ACCESSORY FOR IMPROVING POSTURE

TECHNICAL FIELD OF THE INVENTION

The present invention relates generally to a brassiere accessory for improving posture, and more specifically, to a brassiere accessory that couples to and between shoulder straps at the posterior portion of a brassiere, which rests against the back of a wearer providing a supportive tension that prevents excessive kyphosis (curvature) of the thoracic spine (upper back) and straightens the back of the user so that the user's posture is improved.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

It is well known that sitting hunched over a desk or work station can lead to persistent slouching—bad posture that may cause problems. Bad posture may force a slouching person's chest muscles to tighten, which can cause excessive kyphosis (curvature) of the thoracic spine (upper back). At the same time, postural muscles in the upper back weaken and loosen. As a result, bad posture can have enduring problems that disseminate to other areas of the body. For example, even though an individual may be relatively inactive from day to day, bad posture can result in serious wear-and-tear (sort of speak) on the individual's spine, shoulders, hips, and knees. This is because bad posture may cause the human structure to misalign and weaken, which leads to back and joint pain, reduced flexibility, and compromised muscles. Bad posture may also cause nerve constriction. For example, as the spine curves excessively over time, resulting subluxations can put pressure on the surrounding spinal nerves. Any nerves that may be resultantly pressured or pinched can cause pain at the neck area, back, as well as other areas throughout the body; this is because the spine is essentially a hub connecting nerves from multiple areas of the human body. Typically, those suffering from these maladies tend to limit their mobility and daily exercise (due to weakness, and to avoid further pain), which furthers their weakened state. Accordingly, bad posture may be a source of problems that limit a person's ability to live a healthy lifestyle.

Several methods and devices have been developed over time to address the problems cause by bad posture, including correcting bad posture via specialized garments. Some of these devices may be worn by both male and female users and comprise of complex vests and straps, or bands meant to provide support to the back and core of the wearer. However, many of these devices require the wearer to put on an additional garment that is typically cumbersome and generally uncomfortable to wear. Moreover, the complex nature of these corrective or postural garments make them undesirable to wear from day to day.

For example, some known complex devices include braces for the upper torso that offers posture support. These braces often include bulky components such as shoulder straps and shoulder pads designed to pull the shoulders back thereby straightening the wearer's posture. To improve on the comfort of wearing such devices, many include padding such as shoulder caps or straps that are lined with silicone or some other material that cushion as well as grip the skin at the area of the pectoral muscles or may be designed to cup the shoulders mechanically. One problem with these devices is that these apparatuses typically cover the entire torso, which limits what the wearer can wear from day to day. Another problem is that these devices are often uncomfortable to wear in spite of their designs attempting to improve comfort to the wearer.

Thus, these designs are often particularly undesirable and uncomfortable to wear. Because correcting or at least improving bad posture requires continuous and daily wear, the undesirability of such devices renders them ineffective for improving bad posture—at least for many individuals that end up not wearing these cumbersome devices on a daily basis.

One solution may be to implement a postural garment into a commonly worn garment. It is well known that brassieres are such garments and it is also known that brassiere makers have attempted to incorporate posture-corrective designs into so called postural bras.

For example, there are sports bras designed to enhance posture and increase breast support for women engaging in athletic activities. These devices typically include certain shoulder harnesses that encircle each shoulder and serves to urge them back. One problem with such devices is that they are similarly complex and cumbersome to wear on a daily basis that is outside of the gymnasium. Moreover, sports bras are not typically compatible with all attire and may be perceived as unprofessional—for example if worn in business environments.

As such, these devices do not solve postural problems for day to day wearers not constantly involved in athletic activities. Admittedly, a person could wear such device underneath their regular clothing, but then the individual would have to wear the same device on a daily basis.

In addition to the problems mentioned above with wearers avoiding complex devices that require daily use, a typical bra wearer may not desire to always wear a sport's bra or another specialized brassiere. To address this issue, other devices have been similarly implemented with every-day bras.

For example, some brassieres have been modified for (in addition to providing support and protecting a woman's breasts), helping prevent and correct a tendency of hyperkyphosis of the back. Such modified brassieres typically include a posterior support component that is integral with the specialized brassiere. The problem with that device is that users must either wear the same device daily, or purchase several of those devices in order to be able to wear a posture corrective device every day. Moreover, wearing such devices precludes a wearer from wearing their favorite brassiere brands, or favorite types of brassieres that a wearer may otherwise choose on a daily basis.

Accordingly, the prior art does not adequately address the persistent problems related to posture-improving devices, particularly posture-improving brassieres. In summation, these problems include but are not limited to: (a) requiring the wearer to put on an additional garment that is typically cumbersome and generally uncomfortable to wear; (b) requiring the wearer to purchase multiple devices; or (c) requiring the wearer to forego wearing their preferred brassieres and typical outfits.

Therefore, there exists a previously unappreciated need for a new and improved brassiere accessory that improves a wearer's posture and does not require a user to wear cumbersome devices, or spend significant resources on additional devices for daily use while having to forego a brassiere of their choosing.

More specifically, there exists a previously unappreciated need for a brassiere accessory that may be worn with virtually any brassier and still provides a support that prevents excessive curvature of the upper back and straightens the back of the user so that the user's posture is improved.

It is to these ends that the present invention has been developed.

SUMMARY OF THE INVENTION

To minimize the limitations in the prior art, and to minimize other limitations that will be apparent upon reading and understanding the present specification, the present invention describes a brassiere accessory for improving posture, which is configured to couple between shoulder straps at the posterior portion of a brassiere and rest against the back of a user. The brassier accessory provides a supportive tension that prevents excessive curvature of the upper back and straightens the back of the user so that the user's posture is improved. Moreover, the tension at the back of the user creates a "reminder" for the user to keep their back in an erect posture.

A brassiere system for improving a wearer's posture, in accordance with an exemplary embodiment of the present invention, comprises: a brassier including a chest band and shoulder straps; and a brassier accessory configured to removably couple to the shoulder straps of the brassier, comprising: a substantially non-elastic posterior support including an adjustor for adjusting the length of the non-elastic posterior support; a first elastic connector including a first fastener coupled to and extending from a first terminal end of the non-elastic posterior support, wherein the first elastic connector is configured to wrap around a portion of a first shoulder strap of the brassiere and secure the brassier accessory to the first shoulder strap; and a second elastic connector including a second fastener coupled to and extending from a second terminal end of the non-elastic posterior support, wherein the second elastic connector is configured to wrap around a portion of a second shoulder strap of the brassiere and secure the brassier accessory to the second shoulder strap.

A brassiere accessory adapted to removably couple to shoulder straps of a brassier for improving the wearer's posture, in accordance with an exemplary embodiment of the present invention, comprises: a substantially non-elastic posterior support including an adjustor for adjusting the length of the non-elastic posterior support; a first elastic connector including a first fastener coupled to and extending from a first terminal end of the non-elastic posterior support, wherein the first elastic connector is configured to wrap around a portion of a first shoulder strap of the brassiere and secure the brassier accessory to the first shoulder strap; and a second elastic connector including a second fastener coupled to and extending from a second terminal end of the non-elastic posterior support, wherein the second elastic connector is configured to wrap around a portion of a second shoulder strap of the brassiere and secure the brassier accessory to the second shoulder strap.

A brassiere accessory adapted to removably couple to shoulder straps of a brassier for improving the wearer's posture, in accordance with another exemplary embodiment of the present invention, comprises: a non-elastic posterior support strap including a slider for adjusting the length of the non-elastic posterior support strap; a first elastic strap including a first snap fastener coupled to and extending from a first rigid connector for connecting the first elastic strap to a first terminal end of the posterior support, wherein the first elastic strap is adapted to wrap around a portion of a first shoulder strap of the brassiere and secure the brassier accessory to the first shoulder strap; and a second elastic strap including a second snap fastener coupled to and extending from a second rigid connector for connecting the second elastic strap to a second terminal end of the posterior support, wherein the second elastic strap is adapted to wrap around a portion of a second shoulder strap of the brassiere and secure the brassier accessory to the second shoulder strap.

A brassiere accessory adapted to removably couple to shoulder straps of a brassier for improving the wearer's posture, in accordance with yet another exemplary embodiment of the present invention, comprises: a non-elastic posterior support strap including a triglide for adjusting the length of the non-elastic posterior support strap; a first elastic strap including a first snap fastener coupled to and extending from a first rigid connector for connecting the first elastic strap to a first terminal end of the posterior support, wherein the first elastic strap is adapted to wrap around a portion of a first shoulder strap of the brassiere and secure the brassiere accessory to the first shoulder strap; and a second elastic strap including a second snap fastener coupled to and extending from a second rigid connector for connecting the second elastic strap to a second terminal end of the posterior support, wherein the second elastic strap is adapted to wrap around a portion of a second shoulder strap of the brassiere and secure the brassier accessory to the second shoulder strap. In such embodiment: the first rigid connector comprises a first d-ring adapted to receive a portion of the first elastic strap on one end of the first d-ring and a portion of the first terminal end of the posterior support on the other end of the first d-ring; the second rigid connector comprises a second d-ring adapted to receive a portion of the second elastic connector on one end of the second d-ring and a portion of the second terminal end of the posterior support on the other end of the second d-ring; the first elastic strap includes: a first rectangular region including a first fastener means; a first trapezoidal region with a terminal end that contours to a curvature of the first d-ring; and a first curved region adapted to wrap around a portion of the first d-ring; and the second elastic strap includes: a second rectangular region including a second fastener means; a second trapezoidal region with a terminal end that contours to a curvature of the second d-ring; and a second curved region adapted to wrap around a portion of the second d-ring.

It is an objective of the present invention to provide a brassiere accessory that corrects or improves a wearer's posture.

It is another objective of the present invention to provide a brassiere accessory that encourages proper posture of the wearer.

It is yet another objective of the present invention to provide a brassiere accessory that may be universally worn with any brassiere having shoulder straps.

It is yet another objective of the present invention to provide an accessory that improves a wearer's posture without requiring cumbersome and generally uncomfortable-to-wear garments.

These advantages and features of the present invention are not meant as limiting objectives, but are described herein with specificity to make the present invention understandable to one of ordinary skill in the art.

BRIEF DESCRIPTION OF THE DRAWINGS

Elements in the figures have not necessarily been drawn to scale in order to enhance their clarity and improve understanding of the various embodiments of the invention. Furthermore, elements that are known to be common and well understood to those in the industry are not depicted in order to provide a clear view of the various embodiments of the invention. The drawings that accompany the detailed description can be briefly described as follows.

DETAILED DESCRIPTION OF THE INVENTION

Figure 1:
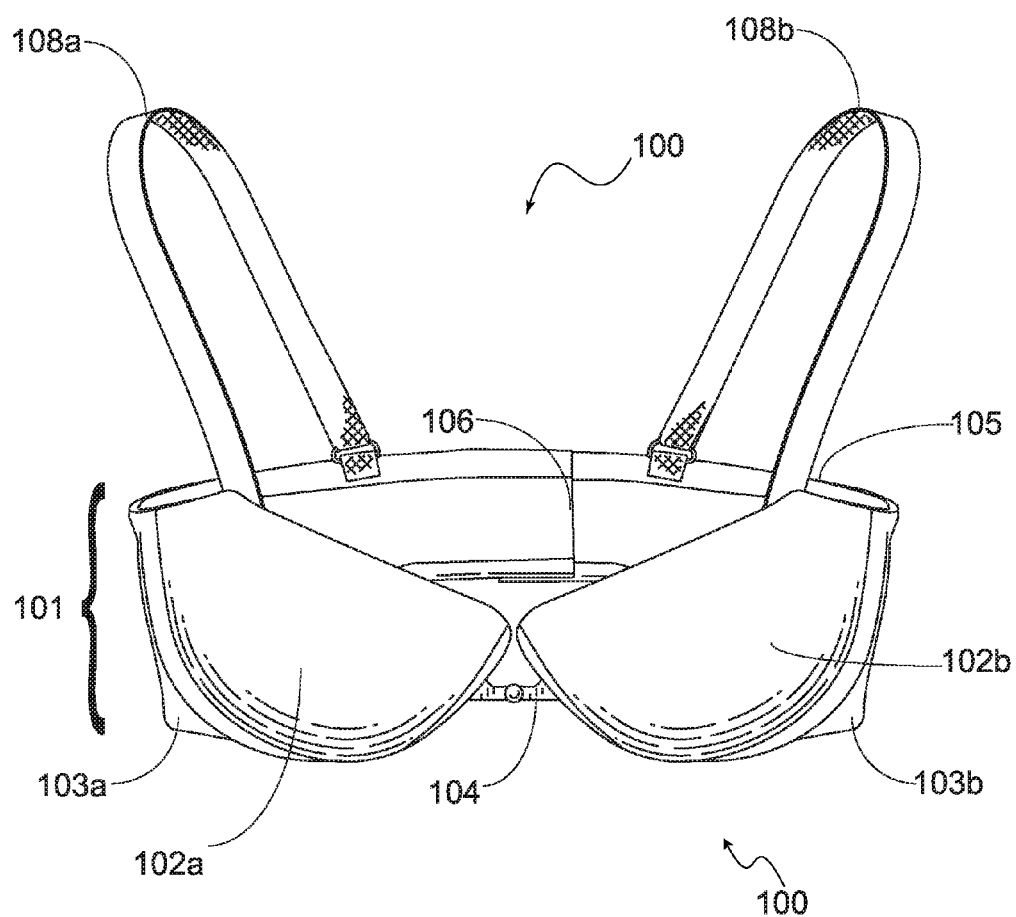
FIG. 1 illustrates a prior art brassiere depicting the various common components of these typical undergarments.

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized and changes may be made without departing from the scope of the invention. Wherever possible, the same reference numbers are used in the drawings and the following description to refer to the same or similar elements. While embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims.

Generally, the invention involves a brassiere accessory that helps to improve a wearer's posture and which may be removably coupled to any brassier that includes shoulder straps. The brassiere accessory couples to the brassiere's shoulder straps in a manner so that the typically flat or planar body of the brassiere accessory rests at the posterior portion of the brassiere flat against the wearer's back and between the shoulder straps of the brassier. The brassiere accessory provides a supportive tension that prevents excessive curvature of the upper back of the wearer and straightens the back of the user so that the user's posture is improved. Moreover, the tension at the back of the user creates a "reminder" for the user to keep their back in a proper erect posture. Because the novel accessory may be used with a variety of brassiere designs that include shoulder straps, a wearer need not wear an additional specialized garment in lieu of their typical brassier. Similarly, a brassier accessory in accordance with the present invention allows users to wear typical clothing as they would normally wear. Because such brassier accessory is removably coupled to a typical brassiere's shoulder straps, a brassier accessory in accordance with the present invention may be universally worn with any brassiere having shoulder straps.

Typically, the main components of common brassieres include a torso component, a pair of cups across the front of the torso component, and shoulder straps connecting the anterior and posterior portions of the torso component. The torso component, which includes the cups adapted to support a wearer's breasts, is typically referred to as the chest band. The chest band may be fastened at a posterior portion or the anterior portion of the brassiere (i.e. bridging the cups together with a fastener or the like). Whether a fastener is implemented at the anterior portion of the chest band, or at the posterior portion of the chest band, the section that connects the cups is typically referred to as a center front gore, or the bridge. The sections connecting either side of the cups with the posterior portion of the chest band are referred to as the wings. The posterior end of the chest band is most often coupled together with what is commonly referred to as a hook-and-eye closure. The shoulder straps are typically permanently attached to a front portion of the chest band, for example at the apex of each of the cups of the brassier.

For illustrative purposes, FIG. 1 illustrates a prior art brassiere depicting the various common components of these typical undergarments. More specifically, FIG. 1 depicts a common brassiere or bra 100, which includes several typical components: mainly, a body, or chest band 101, which includes cups 102a and 102b, wings 103a and 103b, bridge 104, and perimeter 105, which substantially wraps around a wearer's torso. Cups 102a and 102b include an apex region, or apex regions 105a and 105b, and make up the front portion of chest band 101 from a bottom portion to the neckline of bra 100. Typically, bra 100 includes shoulder straps 108a and 108b, which help support the cups. As shown, chest band 101 of bra 100 includes the anterior portion comprising the cups, neckline and bridge, and a posterior portion connected to the anterior portion via perimeter 105, which runs atop of chest band 101. Furthermore, between either side of brassiere 100, wings 103a and 103b connect the anterior and posterior portions to form the tubular body or chest band 101 of bra 100. At the posterior portion of chest band 101, fastening mechanism 106 secures chest band 101 at the back of the wearer.

Different types of materials are often used and thus bra 100 may be constructed of any number of materials without deviating from the scope of the present invention. For example, and without limitation, chest band 101 may comprise linen, cotton broadcloth, twill weaves tricot, spandex, lycra, elastane, latex, microfibers, satin, jacquard weaving, foams, mesh, lace, or any other natural or synthetic fibers with some degree of desirable elasticity. Cups 102a and 102b are typically constructed of varying materials well known in the art. Cups 102a and 102b may include an underwire for added support, as is typically implemented within an inner cavity formed by a plurality of layers of fabric that encapsulate the underwire. Cups 102a and 102b may include padding, or may exclude padding altogether.

Figure 2:
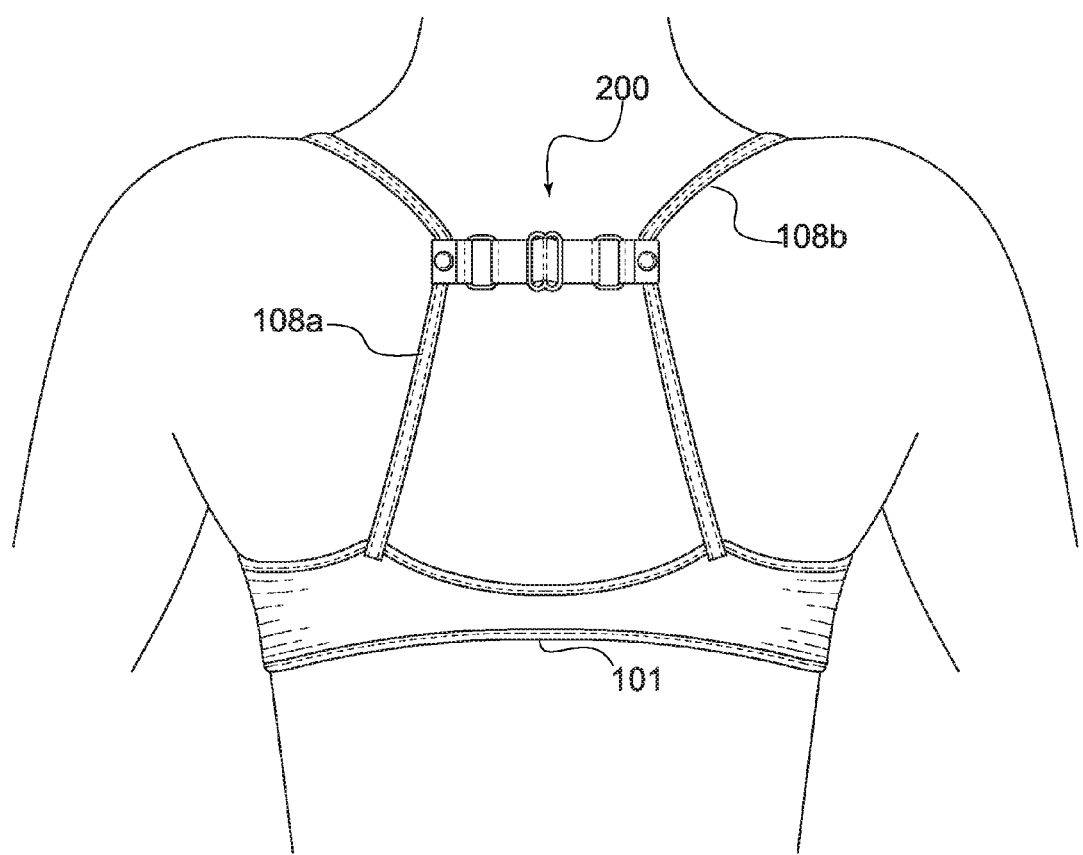
FIG. 2 illustrates a system for improving a brassiere wearer's posture, in accordance with an exemplary embodiment of the present invention.

As with most brassieres such as bra 100, these undergarments are not typically adapted to improve the wearer's posture. Accordingly, a brassiere accessory in accordance with the present invention, may be implemented with known brassieres such as bra 100 to correct or improve the wearer's posture. Turning now to the figures disclosing the present invention, FIG. 2 illustrates a system in accordance with an exemplary embodiment of the present invention specifically depicting brassier accessory 200.

Brassier accessory 200 is typically configured to removably couple to shoulder straps 108a and 108b of bra 100 (or any other brassiere design that includes shoulder straps). In exemplary embodiments, such as the embodiment illustrated in FIG. 2, brassiere accessory 200 comprises a substantially rigid planar body or non-elastic posterior support that may be adjusted to suit a desired length of the brassier accessory.

So that the brassier accessory does not unnecessarily constrict movement—especially as the wearer naturally moves their body—brassiere accessory 200 includes a flexible or elastic element in addition to the more rigid planar body or non-elastic posterior support structure. The elastic element or set of elastic connectors (that will be discussed below) expand and contract between the shoulders of the wearer and along with the shoulder straps of the wearer's brassiere, while the more rigid non-elastic posterior support provides a constant tension (or limited inward pulling between the wearer's shoulders) that enables the wearer to push their chest forward and generally maintain an erect posture.

Accordingly, brassier accessory 200 may include elastic components that couple to and extend from terminal ends of the posterior support, wherein the elastic components are configured to wrap around a portion of each shoulder strap in a manner so that the non-elastic planar body of brassier accessory 200 is generally flat against the wearer's back generally perpendicular to the length of each shoulder strap and substantially parallel to the brassiere's chest band 101. Each component of brassier accessory 200 will be described in more detail below with reference to the remaining figures.

Figure 3:
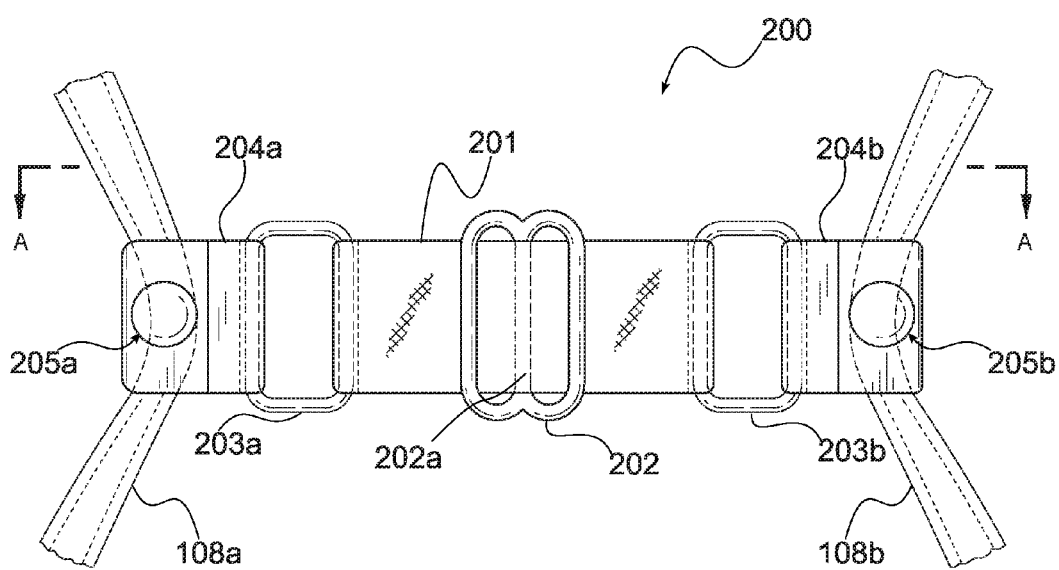
FIG. 3 illustrates a close-up view of the exemplary embodiment of a brassiere accessory depicted in FIG. 2.

Turning to the next figure, FIG. 3 illustrates a close-up view of the exemplary embodiment of a brassiere accessory depicted in FIG. 2. More specifically, various components of brassier accessory 200 are depicted including posterior support 201, adjustor 202, rigid connectors 203a and 203b, elastic connectors 204a and 204b each with fasteners 205a and 205b (respectively), which create channels 206a and 206b (respectively) wherein brassier accessory 200 may retain each shoulder strap 108a and 108b (respectively) therein.

Posterior support 201 typically comprises a generally rigid or non-elastic body that may be substantially flat or planar so as to rest flat against the back of a wearer. In exemplary embodiments, the substantially flat or planar body may comprise a non-elastic band or strap that restricts brassier accessory 200's motion. Its rigidity or lack of elasticity provides a desirable tension (or limited inward pulling) between the wearer's shoulders (center to the wearer's shoulder sockets) at the upper back, which helps the wearer straighten their chest and serves in part as a tension reminder to the wearer to keep an erect posture. This tension naturally prevents excessive hunching or slouching. Posterior support 201 may be constructed as a substantially flat or planar strap constructed of strong durable lightweight material with none or little elasticity so that it is substantially non-elastic. In exemplary embodiments, posterior support 201 is constructed of cotton or flax woven as a flat strip. In other embodiments, posterior support 201 may be constructed of synthetic fibers such as nylon, polypropylene or polyester.

Additionally, in exemplary embodiments, posterior support 201 is adjustable in length so that a single device may be universally used by various sized wearers. Moreover, adjustability allows a wearer to adjust a desired tension that may be suitable for correcting or improving their posture.

Adjustor 202 may be any component that adjusts a length of posterior support 201. Accordingly, adjustor 202 may be a separate component (i.e. as shown in FIG. 3) or more integral component of posterior support 201 so long as it is configured to enable the adjustment of a length of posterior support 201. For example, and without limiting the scope of the present invention, in exemplary embodiments adjustor 202 may be a slide component such as a triglide that is implemented with posterior support 201. In such embodiment, posterior support 201 may comprise a strap of nylon or similarly strong webbing. In such embodiment, adjustor 202 may be coupled to posterior support 201 in a manner so that sliding adjustor 201 along a length of posterior support 201 may lengthen or shorten a length of brassier accessory 200.

Alternatively, adjustor 201 may be a more integral component of posterior support 201; for example, adjustor 202 may comprise of a Velcro™ component implemented on the webbing or strap that may form posterior support 201 (not shown) that secures posterior support 201 at a desired length. In other embodiments, adjustor 202 may include button fasteners or snap fasteners (not shown) that secure posterior support 201 at a desired length. As will be explained further below with reference to remaining figures, implementing an embodiment of adjustor 202 as shown in FIG. 3 may be desirable for ease of use by a wearer as well as for minimizing any bulk that may be undesirable for such an accessory worn with a brassier.

Rigid connectors 203a and 203b may be coupled to and extend from terminal ends of posterior support 201. Rigid connectors 203a and 203b are typically non-elastic and constructed of a rigid, strong and durable material such as lightweight metals or plastics. Typically, rigid connectors 203a and 203b may be substantially flat or comprise a similar thickness as that of posterior support 201 so that brassier accessory 200 may rest at a wearer's back without adding unnecessary bulk. In exemplary embodiments (as shown in FIG. 3), each rigid connector 203a and 203b may comprise a loop or a substantially flat loop-shaped body adapted to receive a terminal end or portion of posterior support 201 on one end of the loop or loop-shaped body, and adapted to receive a terminal end or portion of one of the elastic connectors 204a or 204b on the other one end of the loop or loop-shaped body. In exemplary embodiments rigid connectors 203a and 203b are constructed of plastics. In other exemplary embodiments rigid connectors 203a and 203b are constructed of light weight metal.

In alternative embodiments, brassier accessory 200 may not include rigid connectors at all, and may instead include elastic connectors, which are directly attached to posterior support 201—for example by stitching each elastic connector directly to a terminal end or portion of posterior support 201. However, there are multiple benefits to including rigid connectors 203a and 203b. For example, and without limiting the scope of the present invention, each rigid connector (203a or 203b) creates a secured support structure that enhances the accessory's durability. Moreover, rigid connectors (203a and 203b) allow for implementation of an adjustor—such as adjustor 202 as illustrated in the figures—which facilitates adjustability by allowing a portion of posterior support 201 to slide between a shorter and longer length of posterior support 201 (see FIG. 4 for example).

Elastic connectors 204a and 204b typically extend from the terminal ends of rigid connectors 203a and 203b or from terminal ends of posterior support 201, wherein each of the elastic connectors is configured to wrap around a portion of a shoulder strap of a brassiere and secure brassier accessory 200 to each shoulder strap. Typically, elastic connectors 204a and 204b each include a fastening mechanism such as fastener buttons or snap buttons 205a and 205b (respectively). In exemplary embodiments that implement rigid connectors 203a and 203b—as illustrated by FIG. 3—each elastic connector 204a and 204b is coupled to a terminal end or portion of one of rigid connectors 203a or 203b. Materials utilized for constructing elastic connectors 204a and 204b may include any variety of elastic fibers or elastic construction including braided elastics constructed of latex rubber with fiber coverings comprising either cotton elastic, polyester elastic, nylon elastic or any combination of these or other constructions thereof. Typically, braided elastics are desirable because such construction allows elastic connectors 204a and 204b enhanced memory or stretch retention. Alternatively, elastic connectors 204a and 204b may be constructed of other elastic materials or constructions such as knitted elastics, or any other elastic construction so long as each elastic connector 204a and 204b has a suitable durability and strength for daily wear.

Fasteners 205a and 205b may be any type of fastening mechanism that is implemented with each elastic connectors 204a and 204b. In exemplary embodiments, fasteners 205a and 205b may include a snap button fastener that may be easily snapped together or removed by a wearer, each fastener situated at a terminal end of each elastic connectors 204a and 204b. Alternatively, and without limiting the scope of the present invention, other fastening mechanisms may be implemented with each elastic connectors 204a and 204b— for example each elastic connectors 204a and 204b may include Velcro™ components, other hook and loop mechanisms, or another fastening means such as clasps or the like.

Figure 4:
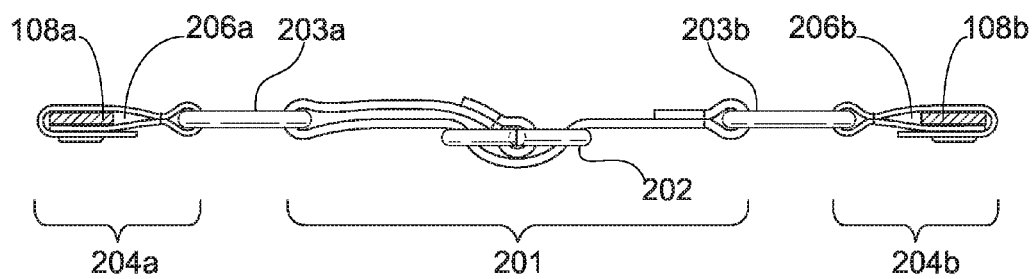
FIG. 4 illustrates a top view of an exemplary embodiment of the brassiere accessory.

Regardless of the construction of elastic connectors 204a and 204b, in exemplary embodiments each elastic connector is configured to wrap around and secure to a shoulder strap of a brassier. For example, as illustrated in FIG. 4, when in a fastened or closed configuration, elastic connectors 204a and 204b form channels 206a and 206b (respectively), which are adapted to receive or envelope a portion of shoulder straps 108a and 108b (respectively). Channels 206a and 206b are depicted in the next figure, which illustrates brassier accessory 200 from a top view along line A.

FIG. 4 illustrates a top view of an exemplary embodiment of the brassiere accessory. More specifically, FIG. 4 illustrates how components of brassier accessory 200, including an exemplary embodiment of posterior support 201, adjustor 202, rigid connectors 203a and 203b, and elastic connectors 204a and 204b, are coupled together to form the brassier accessory. In this top view, the brassier accessory is shown fastened so that shoulder straps 108a and 108b are secured within channels 206a and 206b formed by elastic connectors 204a and 204b. Similarly, FIG. 5 illustrates a top view of the exemplary embodiment of brassiere accessory 200; in this figure, the brassiere accessory shown with each elastic connector 204a and 204b unfastened.

Figure 5:
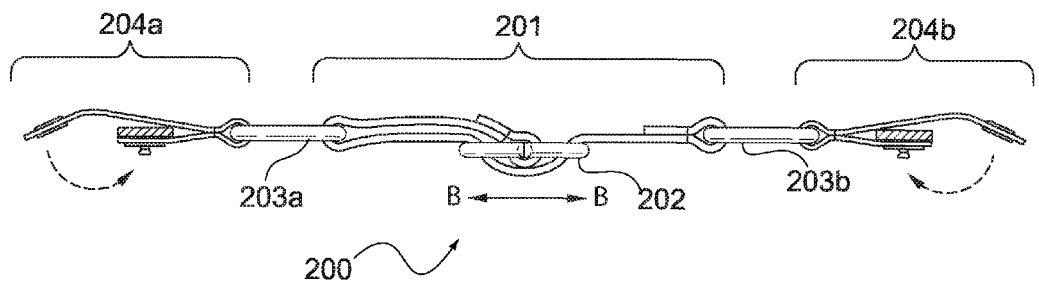
FIG. 5 illustrates a top view of an exemplary embodiment of the brassiere accessory, which may be removably coupled to a brassiere's shoulder straps; the brassiere accessory shown unfastened.

As may be appreciated from FIG. 5, to secure the shown exemplary embodiment to a brassier such as bra 100, a user need only stretch each elastic component slightly to wrap around a portion of the brassiere's shoulder straps 108a and 108b. To adjust a length of posterior support 201 in the shown exemplary embodiment, a user need only slide adjustor 202 in either direction along line B. For example, in order to shorten posterior support 201, adjustor 202 may be slid towards elastic component 204b. Similarly, in order to lengthen posterior support 201, adjustor 202 may be slid towards elastic component 204a. This adjustability is possible in the shown embodiment by posterior support 201 as will be explained in more detail with reference to FIG. 8.

Figure 6:
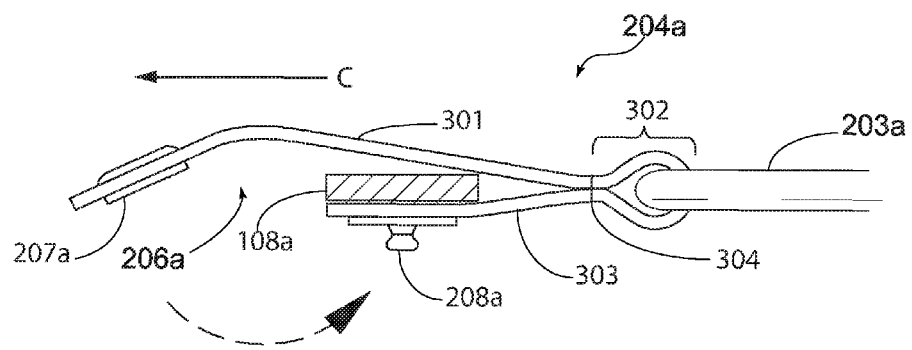
FIG. 6 illustrates a close-up view of an elastic connector of the brassier accessory (in an unfastened or open configuration), in accordance with an exemplary embodiment of the present invention.

Turning to the next figure, FIG. 6 illustrates a close-up view of elastic connector 204a of the brassier accessory (in an unfastened or open configuration), in accordance with the exemplary embodiment illustrated by FIG. 5. More specifically, FIG. 6 shows several components of elastic connector 204a including elastic strap 301 with anchored or secured portion 302 and fastening section 303.

In such exemplary embodiment, elastic strap 301 makes up the body of elastic connector 204a. In order to configure elastic strap 301 for wrapping or enveloping a portion of shoulder strap 108a, elastic strap 301 may be secured to posterior support 201 so that channel 206a may be formed when the elastic strap 301 is looped and fastened to itself. In exemplary embodiments, elastic strap 301 may be secured to posterior support 201 by anchoring a portion thereof (i.e. secured portion 302) to rigid connector 203a. Without deviating from or limiting the scope of the present invention in any way, securing elastic strap 301 to posterior support 201 may be achieved by securely stitching (304) a secured portion 302 of elastic strap 301 that has been wrapped around rigid connector 203a. Of course, other means may be implemented such as using staple means, adhesives, or the like. To enable a user to securely fasten and unfasten elastic connector 204a, elastic strap 301 may include fastener 205a. As shown, fastener 205a includes a female fastening component 207a situated at a terminal end of elastic strap 301, which is configured to register with a male component 208a situated at the other terminal end of elastic strap 301. In exemplary embodiments, the male fastening component extends from a surface 303 of elastic strap 301 that is opposite to the inner surface forming channel 206a so that shoulder strap 108a of bra 100 may be secured therein without obstruction from the same.

Typically, although not necessarily, elastic connector 204b is identical or substantially similar to elastic connector 204a and includes the same components. Because it is elastic, elastic strap 301 may be stretched in the direction along line C (as mentioned above) so that a user need only stretch the elastic component slightly to wrap around a portion of the brassiere's shoulder strap 108a. Once a portion of shoulder strap 108a is enveloped by or within channel 206a, the user or wearer may fasten or register female component 207a with male component 208a of fastener 205a thereby securing brassier accessory 200 to the bra.

Figure 7:
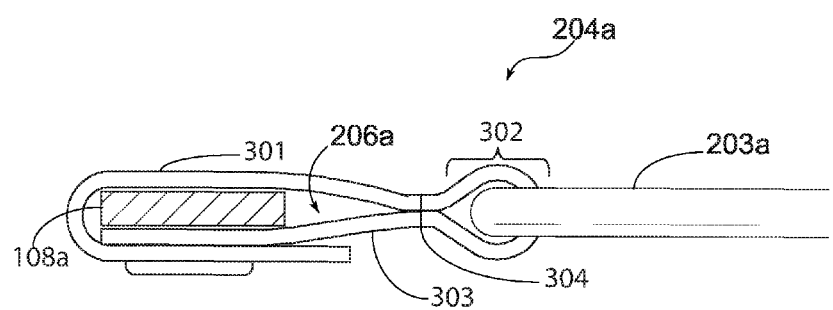
FIG. 7 illustrates a close-up view of an elastic connector of the brassier accessory (in a fastened or closed configuration), in accordance with an exemplary embodiment of the present invention.

FIG. 7 illustrates a close-up view of elastic connector 204a of the brassier accessory (in a fastened or closed configuration), in accordance with the exemplary embodiment discussed above with reference to FIG. 5 and FIG. 6. One function of the elastic connectors is to provide for non-slippage. Accordingly, in alternative exemplary embodiments it is possible to implement non-elastic versions of elastic connectors 204a and 204b. In such embodiment, a component such as elastic strap 301 may be replaced by a non-elastic strap. The non-elastic strap may be constructed of or include a portion comprising rubber or silicone, as is typically found in non-slip garments such as certain hosiery or undergarments. For example, and without limiting the scope of the present invention, the non-slip portion may be implemented in the interior portion of strap 301 so that it encompasses the inner surface of strap 301 that forms channel 206a; this provides similar non-slip functionality that keeps brassiere accessory 200 from slipping down towards chest band 101.

Figure 8:
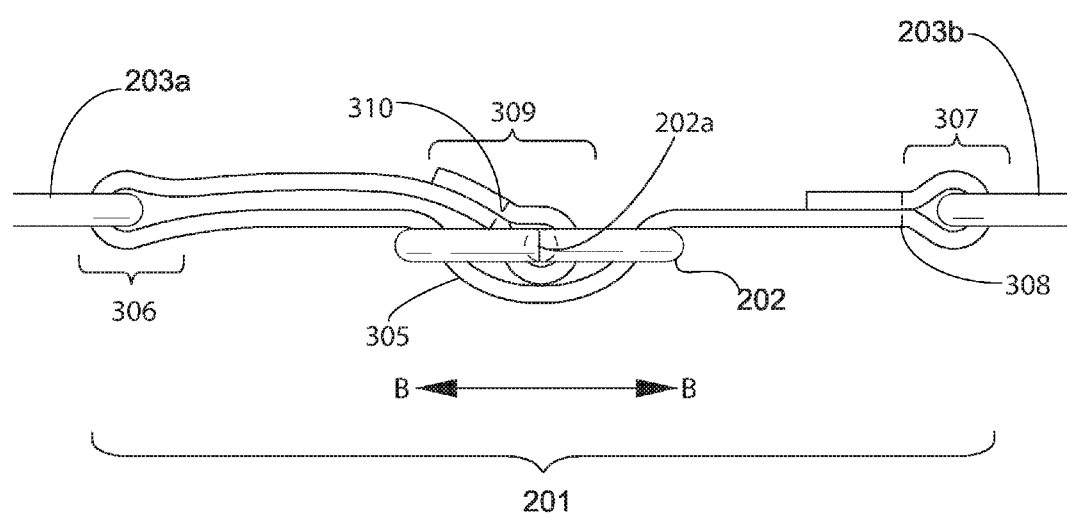
FIG. 8 illustrates a close-up view of a non-elastic posterior support for a brassier accessory in accordance with an exemplary embodiment of the present invention.

Turning now to FIG. 8 a close-up view of a non-elastic posterior support 201 for a brassier accessory in accordance with an exemplary embodiment of the present invention is illustrated. More specifically, FIG. 8 depicts an exemplary embodiment of posterior support 201 that comprises non-elastic strap 305, which has been adapted to be adjusted with adjustor 202 in the manner mentioned above. Non-elastic strap 305, in such embodiment, may be wrapped around a terminal end of rigid connector 203a thereby forming a terminal end 306, which is allowed to remain unsecured so that non-elastic strap 305 may be adjusted in length. This is naturally achieved by threading non-elastic strap 305 through adjustor 202 so that a front portion of the strap is above or in front of center bar 202a of adjustor 202. A second terminal end of non-elastic strap 305 may be wrapped around a terminal end of rigid connector 203b thereby forming a terminal end 307. Because the strap may be adjustable in such embodiment, terminal end 307 is typically secured, for example by securely stitching (308) a secured portion 307 of non-elastic strap 305 that has been wrapped around rigid connector 203b. Moreover, another terminal end 309 of non-elastic strap 305 is typically secured to center bar 202a of adjustor 202; that is, terminal end 309 is typically secured, for example, by securely stitching (310) a secured portion 309 of non-elastic strap 305 that has been wrapped around center bar 202a of adjustor 202. This configuration enables posterior support 201 to be adjusted in length as described above and shown in the figures.

Figure 9:
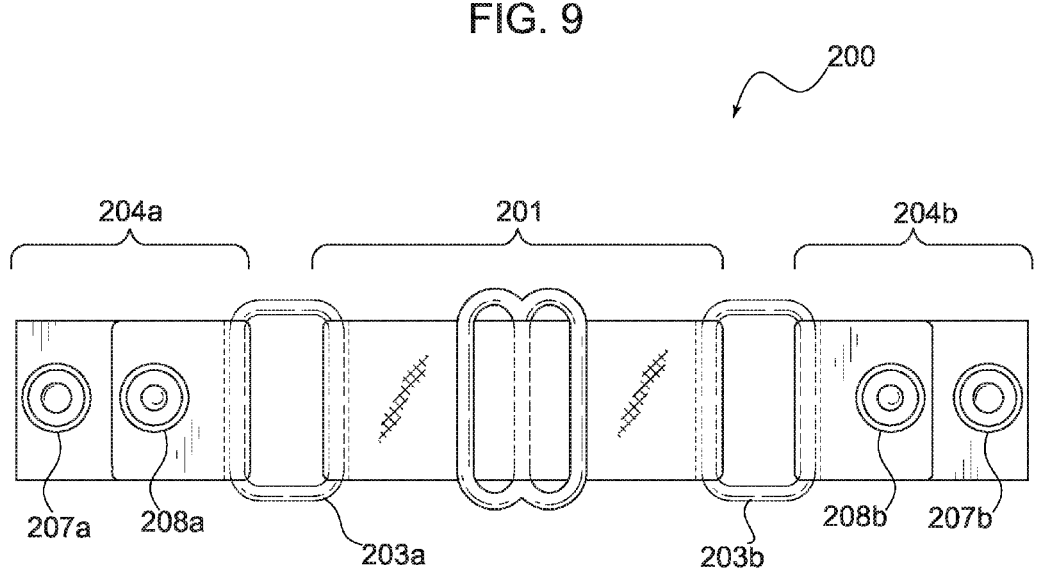
FIG. 9 illustrates a front view of an exemplary embodiment of the brassiere accessory, which may be removably coupled to a brassiere's shoulder straps; the brassiere accessory shown unfastened.
Figure 10:
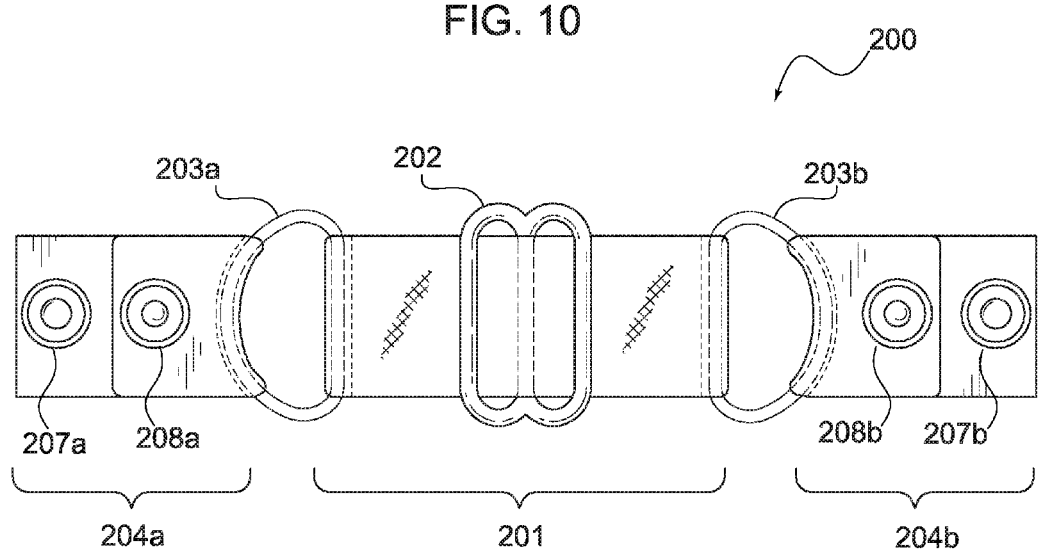
FIG. 10 illustrates a front view of another exemplary embodiment of a brassiere accessory in accordance with the present invention.

Turning now to the remaining figures, FIG. 9 illustrates a front view of an exemplary embodiment of the brassiere accessory (shown unfastened), which may be removably coupled to a brassiere's shoulder straps; and FIG. 10 illustrates a front view of another exemplary embodiment of a brassiere accessory (shown unfastened) in accordance with the present invention. More specifically, FIG. 9 depicts the exemplary embodiment shown in the previous figure, depicting female and male fastening components 207a, 208a, 207b, and 208b. FIG. 10 illustrates another embodiment wherein rigid connectors 203a and 203b include d-rings rather than substantially rectangular loops. One benefit of implementing d-rings rather than substantially rectangular loops may be to permit a wider terminal structure such that either elastic or non-elastic connectors may fan out from the non-elastic strap; an example of an embodiment of the present invention, wherein elastic connectors fan outwards, is illustrated and described in turn with reference to FIG. 11.

Figure 11:
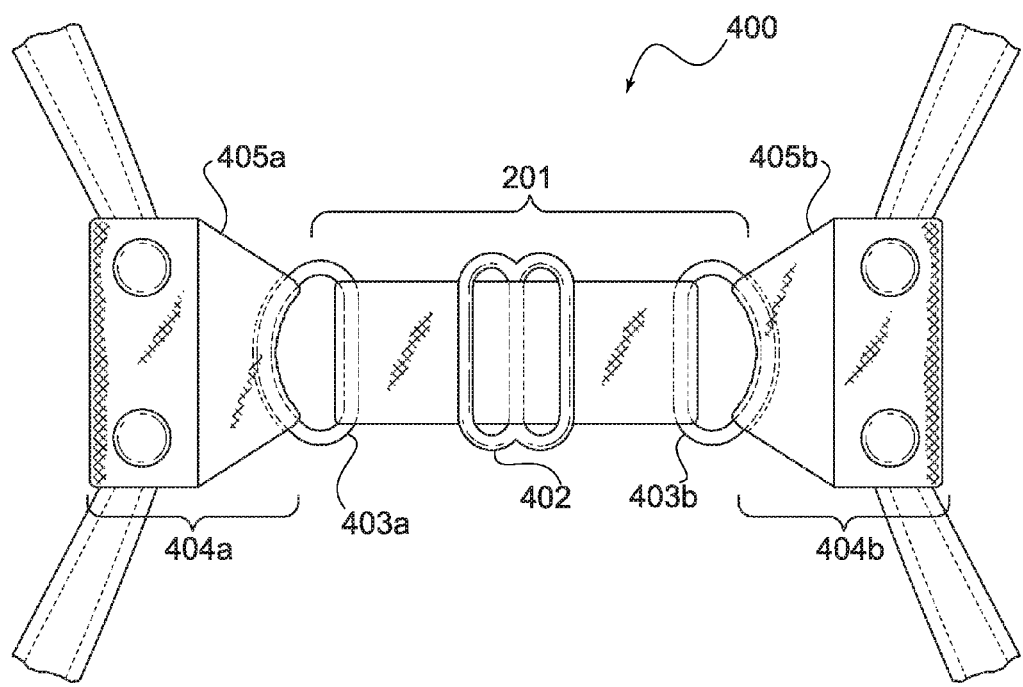
FIG. 11 illustrates a front view of yet another exemplary embodiment of a brassiere accessory in accordance with the present invention.

FIG. 11 illustrates a front view of yet another exemplary embodiment of a brassiere accessory in accordance with the present invention. More specifically, FIG. 11 depicts brassiere accessory 400, which includes posterior support 401 comprising adjustor 402. In this embodiment, rigid connectors 403a and 403b are d-rings, and elastic connectors 404a and 404b fan outwards. Rigid connectors 403a and 203b preferably include d-rings because d-rings are better suited to allow for a wider structure of elastic connectors 404a and 404b. A wider structure means that a greater surface area is created for interaction with each brassiere strap (e.g. 108a and 108b), since the channels created therein (for example channel 206a and channel 206b) are longer.

In such embodiment, elastic connectors 404a and 404b each comprise of an elastic strap 405a and 405b (i.e. similar to strap 301) that makes up the body of each of elastic connectors 404a and 404b. Each elastic strap 405a and 405b for wrapping or enveloping a portion of shoulder strap 108a may be secured to posterior support 401 so that channels may be formed when the elastic straps 405a and 405b are looped and fastened to themselves. Rather than having a generally planar and rectangular structure (as with strap 301), each strap 405a and 405b may include a planar structure with widening trapezoidal portions.

Figure 12:
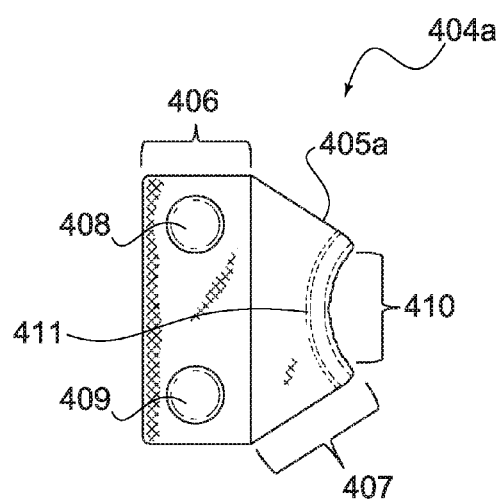
FIG. 12 depicts a close-up view of an elastic connector in accordance with an exemplary embodiment of the present invention.

FIG. 12 depicts a close-up view of elastic connector 404a. Elastic connector 404a includes, as mentioned above, strap 405a. Strap 405a may exemplarily include three different regions when coupled together to itself (i.e. such as strap 301 shown in FIG. 7). A first region may be a rectangular region 406, which includes a fastening means such as fasteners 408 and 409. A second region may be a trapezoidal region 407, which includes a first terminal end that is longer than a second terminal end, wherein the second terminal end wraps around a portion of rigid connector 403a. A third region 410 is a curved region which secures strap 405a of elastic connector 404a to rigid connector 404a. Region 410 may be secured to rigid connector 404a in a similar manner as implemented with strap 301 using stitching or an adhesive or any other means of securing a portion of rigid connector 403a. In exemplary embodiments, stitching 411 is implemented in a manner so that the stitching curves or contours to a curvature of rigid connector 403a.

As may be appreciated from the discussion above, other alternatives and variations of the illustrated embodiments are possible without deviating from the scope of the present invention.

A brassiere with removable shoulder straps has been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

DESCRIPTION OF THE REFERENCE SYMBOLS

100: Bra (Prior Art)
101: Chest band
102a: Cup
102b: Cup
103a: Wing
103b: Wing
104: Bridge
105: Perimeter
106: Fastening mechanism
108a: Shoulder strap
108b: Shoulder strap
200: Brassier accessory
201: Posterior support
202: Adjustor
202a: Center support
203a: Rigid connector
203b: Rigid connector
204a: Elastic connector
204b: Elastic connector
205a: Fastener
205b: Fastener
206a: Channel
206b: Channel
207a: Fastener component
207b: Fastener component
208a: Fastener component
208b: Fastener component
301: Elastic strap (of elastic connector)
302: Secured portion (of elastic connector)
303: Section (of elastic connector)
304: Stitching (of elastic connector)
305: Non-elastic strap (of posterior support)
306: Terminal end (of posterior support)
307: Terminal end (of posterior support)
308: Stitching (of posterior support)
309: Securing means (of posterior support)
310: Securing means (of posterior support)
400: Brassier accessory
401: Posterior support
402: Adjustor
403a: Rigid connector
403b: Rigid connector
404a: Elastic connector
404b: Elastic connector
405a: Strap
405b: Strap
406: Region
407: Region
408: Fastener
409: Fastener
410: Region
411: Stitching

What is claimed is:

1. A brassiere system for improving a wearer's posture, comprising:
a brassiere including a chest band and shoulder straps; and
a brassiere accessory configured to removably couple to the shoulder straps of the brassiere, comprising:
a substantially non-elastic posterior support including an adjustor for adjusting a length of the substantially non-elastic posterior support;
a first elastic connector including a first fastener coupled to and extending from a first terminal end of the substantially non-elastic posterior support, wherein the first elastic connector is configured to wrap around a portion of a first shoulder strap of the brassiere and secure the brassiere accessory to the first shoulder strap; and
a second elastic connector including a second fastener coupled to and extending from a second terminal end of the substantially non-elastic posterior support, wherein the second elastic connector is configured to wrap around a portion of a second shoulder strap of the brassiere and secure the brassiere accessory to the second shoulder strap.

2. The system of claim 1, further comprising:
a first rigid connector for connecting the first elastic connector to the first terminal end of the substantially non-elastic posterior support; and
a second rigid connector for connecting the second elastic connector to the second terminal end of the substantially non-elastic posterior support.

3. The system of claim 2, wherein:
the first rigid connector comprises a first loop adapted to receive a portion of the first elastic connector on a first end of the first loop, and a portion of the first terminal end of the substantially non-elastic posterior support on a second end of the first loop; and
the second rigid connector comprises a second loop adapted to receive a portion of the second elastic connector on a first end of the second loop, and a portion of the second terminal end of the substantially non-elastic posterior support on a second end of the second loop.

4. The system of claim 3, wherein the first and second loops comprise of substantially rectangular loops.

5. The system of claim 3, wherein the first and second loops comprise of a first and a second D-rings.

6. The system of claim 3, wherein the first and second elastic connectors comprise of elastic straps.

7. The system of claim 3, wherein the adjustor comprises a triglide.

8. The system of claim 7, wherein the first and second fasteners comprise of snap fasteners.

9. The system of claim 7, wherein the substantially non-elastic posterior support comprises a strap including stitching.

10. A brassiere accessory adapted to removably couple to shoulder straps of a brassiere for improving a wearer's posture, comprising:
a substantially non-elastic posterior support including an adjustor for adjusting a length of the substantially non-elastic posterior support;
a first elastic connector including a first fastener coupled to and extending from a first terminal end of the substantially non-elastic posterior support, wherein the first elastic connector is configured to wrap around a portion of a first shoulder strap of the brassiere and secure the brassiere accessory to the first shoulder strap; and
a second elastic connector including a second fastener coupled to and extending from a second terminal end of the substantially non-elastic posterior support, wherein the second elastic connector is configured to wrap around a portion of a second shoulder strap of the brassiere and secure the brassiere accessory to the second shoulder strap.

11. The brassiere accessory of claim 10, further comprising:

a first rigid connector for connecting the first elastic connector to the first terminal end of the substantially non-elastic posterior support; and a second rigid connector for connecting the second elastic connector to the second terminal end of the substantially non-elastic posterior support.

12. The brassiere accessory of claim 11, wherein:

the first rigid connector comprises a first substantially rectangular loop adapted to receive a portion of the first elastic connector on a first end of the first substantially rectangular loop, and a portion of the first terminal end of the substantially non-elastic posterior support on a second end of the first substantially rectangular loop; and the second rigid connector comprises a second substantially rectangular loop adapted to receive a portion of the second elastic connector on a first end of the second substantially rectangular loop, and a portion of the second terminal end of the substantially non-elastic posterior support on a second end of the second substantially rectangular loop.

13. The brassiere accessory of claim 12, wherein the first and second elastic connectors comprise of elastic straps.

14. The brassiere accessory of claim 13, wherein the first and second fasteners comprise of snap fasteners.

15. The brassiere accessory of claim 10, wherein the substantially non-elastic posterior support comprises a strap.

16. The brassiere accessory of claim 15, wherein the strap comprises webbing.

17. The brassiere accessory of claim 16, wherein the adjustor comprises a slide adjustor coupled to the strap.

18. The brassiere accessory of claim 17, wherein the slide adjustor coupled to the strap comprises a triglide.

19. A brassiere accessory adapted to removably couple to shoulder straps of a brassiere for improving a wearer's posture, comprising:

a non-elastic posterior support strap including a triglide for adjusting a length of the non-elastic posterior support strap;

a first elastic strap including a first snap fastener coupled to and extending from a first rigid connector for connecting the first elastic strap to a first terminal end of the non-elastic posterior support strap, wherein the first elastic strap is adapted to wrap around a portion of a first shoulder strap of the brassiere and secure the brassiere accessory to the first shoulder strap; and a second elastic strap including a second snap fastener coupled to and extending from a second rigid connector for connecting the second elastic strap to a second terminal end of the non-elastic posterior support strap, wherein the second elastic strap is adapted to wrap around a portion of a second shoulder strap of the brassiere and secure the brassiere accessory to the second shoulder strap.

20. The brassiere accessory of claim 18, wherein:

the first rigid connector comprises a first d-ring adapted to receive a portion of the first elastic strap on a first end of the first d-ring and a portion of the first terminal end of the non-elastic posterior support strap on a second end of the first d-ring;

the second rigid connector comprises a second d-ring adapted to receive a portion of the second elastic connector on a first end of the second d-ring and a portion of the second terminal end of the non-elastic posterior support strap on a second end of the second d-ring;

the first elastic strap includes:
- a first rectangular region including the first snap fastener;
- a first trapezoidal region with a terminal end that contours to a curvature of the first d-ring; and
- a first curved region adapted to wrap around a portion of the first d-ring; and the second elastic strap includes:
- a second rectangular region including the second snap fastener means;
- a second trapezoidal region with a terminal end that contours to a curvature of the second d-ring; and
- a second curved region adapted to wrap around a portion of the second d-ring.

* * * * *